US00PP24381P2

(12) United States Plant Patent
Ui

(10) Patent No.: US PP24,381 P2
(45) Date of Patent: Apr. 8, 2014

(54) ***CALIBRACHOA* PLANT NAMED 'SAKCAL105'**

(50) Latin Name: ***Calibrachoa* spp.**
Varietal Denomination: SAKCAL105

(71) Applicant: Sakata Seed Corporation, Yokohama (JP)

(72) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/815,965

(22) Filed: Mar. 19, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Anne Marie Grunberg
*Assistant Examiner* — Keith Robinson
(74) *Attorney, Agent, or Firm* — James M. Weatherly; Cochran Freund & Young LLC

(57) ABSTRACT

A *Calibrachoa* plant particularly distinguished by having a rosy red flower color and a compact plant growth habit, is disclosed.

1 Drawing Sheet

Genus and species: *Calibrachoa* spp.
Variety denomination: 'SAKCAL105'.

BACKGROUND OF THE NEW PLANT

The present invention comprises a new and distinct variety of *Calibrachoa* plant, botanically known as *Calibrachoa* spp., and referred to by the variety name 'SAKCAL105'. 'SAKCAL105' originated from a hybridization in Kakegawa, Japan in 2008 between the female *Calibrachoa* line '7-1A', an unpatented proprietary hybrid *Calibrachoa* breeding line having a scarlet red flower color and mounding growth habit and the male *Calibrachoa* line '6dw-54A-2', an unpatented proprietary hybrid *Calibrachoa* breeding line with a yellow flower color and compact growth habit.

In November 2007, the female parent line '7-1A' and the male parent line '6dw-54A-2' were crossed and 200 seeds were obtained. In February 2008, the $F_1$ seed were sown in a greenhouse, cultivated, and plant lines were produced with flower colors of yellow, rose and purple with compact and mounding growth habits. Two plant lines were selected within the $F_1$ plants that had yellow and purple flowers and a compact plant growth habit. The two plant lines were intercrossed and 900 seeds were obtained.

In July 2008, 600 seeds were sown in the greenhouse, cultivated and plant lines were produced with flower colors of rosy red, yellow, purple and brown and a compact plant growth habit. A single plant was selected within the $F_1$ plants that had a rosy red flower color and a compact growth habit and designated 'K2009-049'.

In February 2009, 'K2009-049' was vegetatively propagated, cultivated, and evaluated. In April 2009, 'K2009-049' was confirmed to be fixed and stable. 'K2009-049' was further propagated and cultivated to reconfirm the line's stability. 'K2009-049' was subsequently designated 'SAKCAL105' and found to have its unique characteristics reproduce true to type in successive generations of asexual vegetative propagation via vegetative cuttings.

SUMMARY

The following are the most outstanding and distinguishing characteristics of this new variety when grown under normal horticultural practices in Salinas, Calif.

1. Rosy red flower color; and
2. A compact plant growth habit.

DESCRIPTION OF THE PHOTOGRAPHS

This *Calibrachoa* plant is illustrated by the accompanying photographs which show the plant's overall plant habit including form, foliage, and flowers. The photographs are of a four-month-old plant grown in Salinas, Calif. under greenhouse conditions in the summer of 2012. The colors shown are as true as can be reasonably obtained by conventional photographic procedures.

DESCRIPTION OF THE NEW VARIETY

Figure 1:
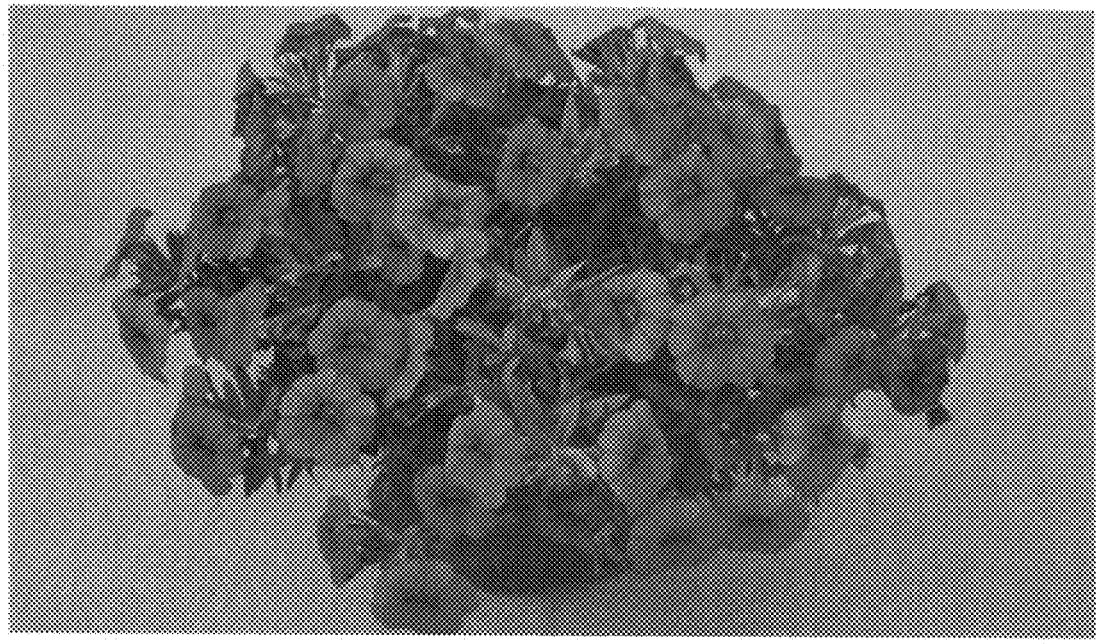
FIG. 1 shows the overall plant habit of the plant grown in a pot.
Figure 2:
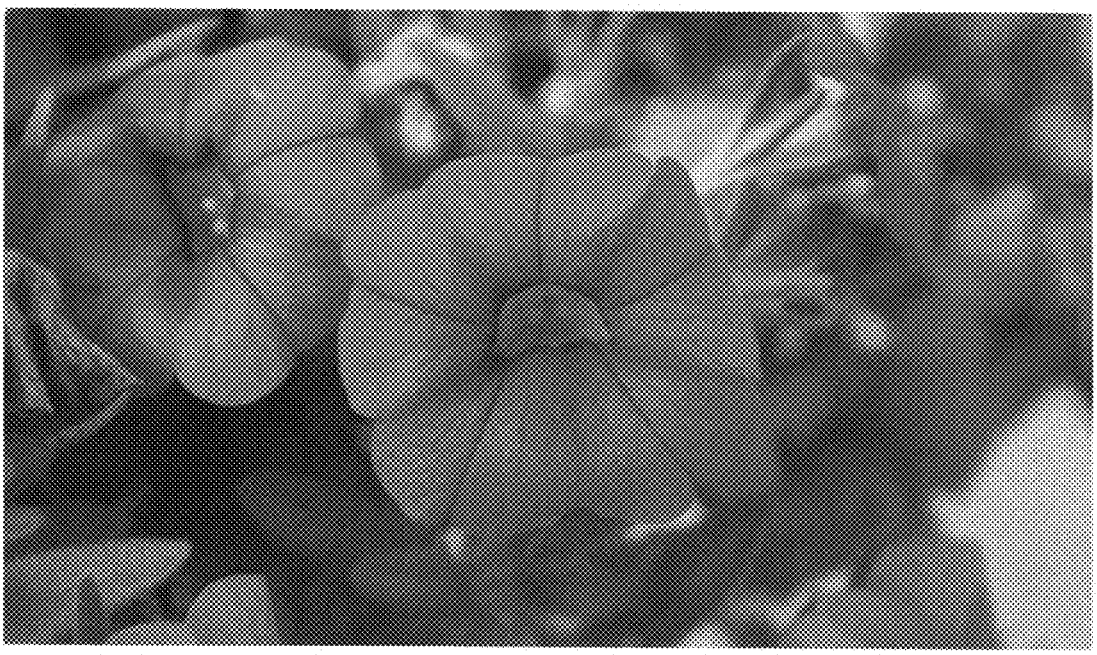
FIG. 2 shows a close-up of the mature inflorescence of the plant.

The following detailed descriptions set forth the distinctive characteristics of 'SAKCAL105'. The data which define these characteristics were collected from asexual reproductions carried out in Salinas, Calif. Data was collected on four-month-old plants grown under greenhouse conditions in Salinas, Calif. in the summer of 2012. Color references are to The R.H.S. Colour Chart of The Royal Horticultural Society of London (R.H.S.), 4$^{th}$ edition (2001).

Classification:

*Family*.—Solanaceae.
*Botanical*.—*Calibrachoa* spp.
*Common*.—*Calibrachoa*.
*Designation*.—'SAKCAL105'.

Parentage:

*Female parent*.—Proprietary hybrid *Calibrachoa* line '7-1A' (unpatented).
*Male parent*.—Proprietary hybrid *Calibrachoa* line '6dw-54A-2' (unpatented).

Growth:

*Time to produce a rooted cutting.*—About 6 weeks.

*Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20-cm diameter plastic pots in a glass greenhouse located in Salinas, California. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit and form.*—Compact and branching.

*Life cycle.*—Tender perennial.

*Height (from soil line to top of foliage).*—7.0 cm.

*Spread.*—30.0 cm.

*Flowering requirements.*—Will flower so long as day length is greater than 12 hours and temperature is above 13° C.

*Temperature tolerances.*—Excellent resistance to rain, heat, and drought. Plants will not tolerate temperatures below 10° C.

Stems:

*General description.*—Circular in cross-section; dull in appearance.

*Stem length.*—12.0 cm.

*Diameter.*—0.15 cm.

*Internode length (average).*—0.5 cm.

*Color.*—RHS 143A (Green).

*Pubescence.*—Slight; pubescence is RHS N155A (White).

*Anthocyanin color.*—Absent.

Leaves:

*Arrangement.*—Alternate.

*Shape.*—Elliptic.

*Apex.*—Obtuse.

*Base.*—Attenuate.

*Margin.*—Entire.

*Surface appearance (both surfaces).*—Dull.

*Surface pubescence (both surfaces).*—Slightly pubescent; pubescence is RHS N155A (White).

*Length.*—2.8 cm.

*Width.*—1.8 cm.

*Color.*—Upper surface: RHS 147A (Yellow-Green). Lower surface: RHS 147B (Yellow-Green).

*Venation.*—Pinnate.

*Petiole.*—Absent; decurrent leaf attachment.

*Fragrance.*—Absent.

Inflorescence:

*Inflorescence type.*—Solitary.

*Flowering habit.*—Indeterminate.

*Time to bloom from propagation.*—10 weeks.

*Lastingness of individual blooms on the plant.*—5 days.

*Fragrance.*—Absent.

Flower bud:

*Surface texture.*—Pubescent.

*Length.*—2.0 cm.

*Diameter.*—0.5 cm.

*Shape.*—Ovate.

*Color.*—RHS 186A (Greyed-Purple).

Peduncle:

*Length.*—0.8 cm.

*Diameter.*—0.1 cm.

*Color.*—RHS 145B (Yellow-Green).

*Surface appearance and texture.*—Dull with heavy pubescence; pubescence color is RHS N155A (White).

Corolla:

*Shape.*—Composed of five, fused petals to create a funnel-shaped flower with five fissures and a shallow, yet prominent, indentation of the petal tip at the midvein.

*Flower diameter.*—3.0 cm.

*Flower depth.*—0.5 cm.

*Petals.*—Shape: Bilabiate. Apex: Truncate. Base: Fused. Margin: Entire. Surface texture (both surfaces): Glabrous. Length: 1.0 cm. Width: 1.5 cm. Color: Upper surface: Closest to RHS 47A (Red). Lower surface: Closest to RHS 186A (Greyed-Purple) with RHS N187A (Greyed-Purple) at midvein. Eye zone: RHS 187A (Greyed-Purple) at petal base.

*Corolla tube.*—Length: 1.0 cm. Diameter: 0.4 cm. Color: Inner surface: RHS 13A (Yellow). Outer surface: Closest to RHS 4B (Yellow).

Calyx:

*Arrangement.*—Composed of 5 sepals, free.

*Sepals.*—Shape: Elliptical. Apex: Obtuse. Margin: Entire. Color (both surfaces): RHS 143A (Green). Length: 1.0 cm. Diameter: 0.2 cm.

Reproductive organs:

*Stamen number.*—5.

*Stamen color.*—RHS 154D (Yellow-Green).

*Stamen form.*—Free.

*Pollen color.*—RHS 10B (Yellow).

*Pollen amount.*—Abundant.

*Ovary.*—Superior.

*Placental arrangement.*—Central.

*Pistil number.*—1 (per inflorescence).

*Pistil length.*—0.7 cm.

*Pistil color.*—RHS 145B (Yellow-Green).

*Stigma color.*—RHS 11A (Yellow).

*Style length.*—1.0 cm.

*Style color.*—RHS 154D (Yellow-Green).

*Seed production.*—Absent.

Disease and insect resistance: Plants are susceptible to *Botrytis*, powdery mildew, various stem and root rots, and certain viruses, such as Tobacco Mosaic Virus and Impatiens Necrotic Spotted Virus. Plants can be infested with aphids, leafminers, whitefly, and various *Lepidoptera*.

COMPARISON WITH PARENTAL LINES AND KNOWN VARIETY

'SAKCAL105' is a new and unique variety of *Calibrachoa* owing to its rosy red flower color and compact plant growth habit. 'SAKCAL105' is distinguished from its parents mainly by flower color as shown in Table 1 below:

TABLE 1

| Comparison with Parental Lines | | | |
|---|---|---|---|
| Characteristic | 'SAKCAL105' | Female Parent '7-1A' | Male Parent '6dw-54A-2' |
| Flower color | Rosy Red | Scarlet Red | Yellow |
| Plant growth habit | Compact | Mounding | Compact |

'SAKCAL105' is a new and unique variety of *Calibrachoa* owing to its rosy red flower color and a compact plant growth habit. 'SAKCAL105' is most similar to the commercial *Calibrachoa* variety 'USCAL128' (U.S. Plant Pat. No. 14,847), commercially known as SUPERBELLS® 'Red'; however there are differences as described in Table 2 below.

TABLE 2

| Comparison with Similar Variety | | |
|---|---|---|
| Characteristic | 'SAKCAL105' | 'USCALI28' |
| Flower petal color, upper surface | Closest to RHS 47A (Red) | RHS 53A (Red) |
| Flower petal color, lower surface | Closest to RHS 186A (Greyed-Purple) with RHS N187A (Greyed-Purple) at midvein | RHS 186A (Greyed-Purple) |
| Flower size (diameter) | 3.0 cm | 2.9 cm |
| Plant growth habit | Compact | Semi-upright |

I claim:

1. A new and distinct variety of *Calibrachoa* plant as shown and described herein.

* * * * *